United States Patent
Fenner et al.

(10) Patent No.: US 10,379,009 B2
(45) Date of Patent: Aug. 13, 2019

(54) SAMPLING POD SYSTEM HAVING REMOVABLE SAMPLING POD WITH LID

(71) Applicant: Sampling Systems Ltd., Warwickshire (GB)

(72) Inventors: Simon Jonathan Fenner, Warwickshire (GB); Jonathan Paul Fenner, Warwickshire (GB); Michael John Fenner, Warwickshire (GB)

(73) Assignee: SAMPLING SYSTEMS LTD., Warwickshire (GB)

( * ) Notice: Subject to any disclaimer, the term of this patent is extended or adjusted under 35 U.S.C. 154(b) by 116 days.

(21) Appl. No.: 15/180,810

(22) Filed: Jun. 13, 2016

(65) Prior Publication Data

US 2016/0363512 A1    Dec. 15, 2016

(30) Foreign Application Priority Data

Jun. 13, 2015   (GB) .................................. 1510388.0

(51) Int. Cl.
*G01N 1/04*   (2006.01)
*G01N 1/08*   (2006.01)
(Continued)

(52) U.S. Cl.
CPC ............... *G01N 1/04* (2013.01); *G01N 1/08* (2013.01); *G01N 1/10* (2013.01); *G01N 1/16* (2013.01);
(Continued)

(58) Field of Classification Search
CPC .. G01N 1/08; G01N 1/18; G01N 1/16; G01N 1/20; G01N 2001/005; G01N 2001/007
See application file for complete search history.

(56) References Cited

U.S. PATENT DOCUMENTS

| | | | | | |
|---|---|---|---|---|---|
| 1,078,847 | A | * | 11/1913 | Grauenfels et al. ..... | G01N 1/12  73/863.31 |
| 1,256,413 | A | * | 2/1918 | Wiswell ................... | G01N 1/08  73/864.64 |

(Continued)

FOREIGN PATENT DOCUMENTS

| | | | | |
|---|---|---|---|---|
| CA | 2272476 A1 | * | 11/2000 | ............... E02D 1/04 |
| CN | 105403436 A | | 3/2016 | |

OTHER PUBLICATIONS

Intellectual Property Office Search Report under Section 17 dated Jul. 27, 2016 regarding application No. GB1510388.0.

(Continued)

*Primary Examiner* — Harshad R Patel
*Assistant Examiner* — Tran M. Tran
(74) *Attorney, Agent, or Firm* — Buchanan Ingersoll & Rooney PC

(57) ABSTRACT

A method of, and apparatus for sampling a solid or liquid sample using a sampling tool which has a sampling rod/tube that is configured to house a sampling pod, the apparatus comprising: a main body portion with at least one sample collecting cavity; and a removable/opening lid portion that in use fits/closes over at least part of said main body portion and thereby covers and the cavity; the method further comprising the following steps: Inserting said sampling pod main body portion within said sampling rod/tube and taking a solid or liquid sample from a vessel/container; removing sampling rod/tube from said vessel or container and covering said collecting cavity to seal said cavity; transporting said sample within said sampling pod to place of a analysis; and at place of analysis removing at least part of said covering from main body portion to expose sample for analysis.

12 Claims, 17 Drawing Sheets

(51) Int. Cl.
  *G01N 1/16* (2006.01)
  *G01N 1/18* (2006.01)
  *G01N 1/10* (2006.01)
  *G01N 1/20* (2006.01)

(52) U.S. Cl.
  CPC ....... *G01N 1/18* (2013.01); *G01N 2001/2071* (2013.01)

(56) References Cited

U.S. PATENT DOCUMENTS

| | | | | |
|---|---|---|---|---|
| 1,780,597 | A * | 11/1930 | Mayhall | G01N 1/12 374/157 |
| 2,968,184 | A * | 1/1961 | Archer | G01N 1/08 73/863.81 |
| 3,091,968 | A * | 6/1963 | Platzer | G01N 1/08 73/863.31 |
| 3,218,869 | A * | 11/1965 | Fields | G01N 1/08 73/863.31 |
| 3,597,980 | A * | 8/1971 | Beuker | G01N 1/08 73/864.51 |
| 3,960,021 | A * | 6/1976 | Jones | G01N 1/12 294/99.1 |
| 4,088,025 | A * | 5/1978 | Foster | G01N 1/08 73/863.33 |
| 4,179,930 | A * | 12/1979 | Chrisp | G01N 1/08 73/864.64 |
| 4,790,198 | A * | 12/1988 | Awtry | G01N 1/08 73/864.64 |
| 4,800,765 | A * | 1/1989 | Nelson | G01N 1/08 73/863.86 |
| 5,179,859 | A * | 1/1993 | Van Niekerk | G01N 1/08 73/864.64 |
| 5,337,620 | A * | 8/1994 | Kalidini | G01N 1/08 73/864.64 |
| 5,440,941 | A * | 8/1995 | Kalidindi | G01N 1/08 73/864.64 |
| 5,442,970 | A * | 8/1995 | Hutchins | G01N 1/12 73/864.63 |
| 5,471,886 | A * | 12/1995 | Kalidindi | G01N 1/08 73/864.63 |
| 5,726,363 | A * | 3/1998 | Kalidindi | G01N 1/14 73/864.13 |
| 5,928,164 | A * | 7/1999 | Burbank | A61B 10/0266 600/567 |
| 5,962,215 | A * | 10/1999 | Douglas | G01N 33/521 422/417 |
| 6,094,999 | A * | 8/2000 | Dubois | G01N 1/08 73/863.31 |
| 6,153,147 | A * | 11/2000 | Craig | B01L 3/5023 422/408 |
| 6,241,687 | B1 * | 6/2001 | Voegele | A61B 10/0266 600/566 |
| 6,318,193 | B1 * | 11/2001 | Brock | G01N 1/08 73/864.74 |
| 6,339,966 | B1 * | 1/2002 | Kalidindi | G01N 1/08 73/864.31 |
| 6,575,303 | B1 * | 6/2003 | Brock | B07B 1/46 209/238 |
| 6,585,507 | B1 * | 7/2003 | Kalidindi | B30B 11/04 425/344 |
| 6,796,194 | B1 * | 9/2004 | Ryan | G01N 1/20 73/290 R |
| 6,835,180 | B2 * | 12/2004 | Rudnick | A61B 10/0096 600/562 |
| 6,862,943 | B2 * | 3/2005 | Tibbets | G01N 1/08 73/864.64 |
| 7,472,614 | B1 * | 1/2009 | Kalidindi | G01N 1/12 73/864.64 |
| 8,770,048 | B2 * | 7/2014 | Khuzwayo | G01N 1/16 73/863.71 |
| 8,911,990 | B2 * | 12/2014 | Samadpour | C12M 1/262 435/309.1 |
| 2003/0205098 | A1 * | 11/2003 | Kalidindi | G01N 1/20 73/863.81 |
| 2011/0000322 | A1 * | 1/2011 | Chen | G01N 1/08 73/864.64 |
| 2011/0244461 | A1 * | 10/2011 | Tanigami | A61B 10/0038 435/6.11 |

OTHER PUBLICATIONS

European Search Report dated Oct. 31, 2016 regarding application No. EP16020227.

* cited by examiner

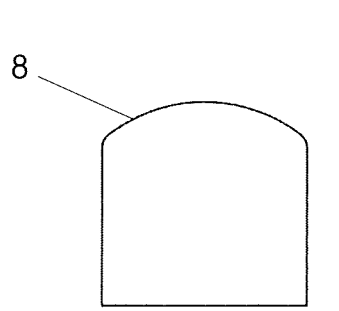
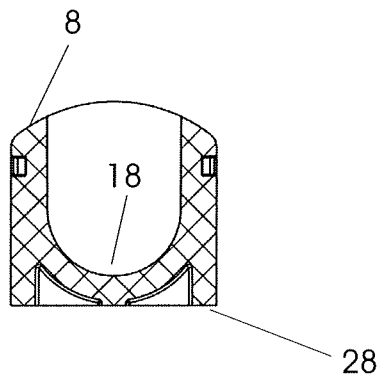
Figure 1(j)          Figure 1(k)
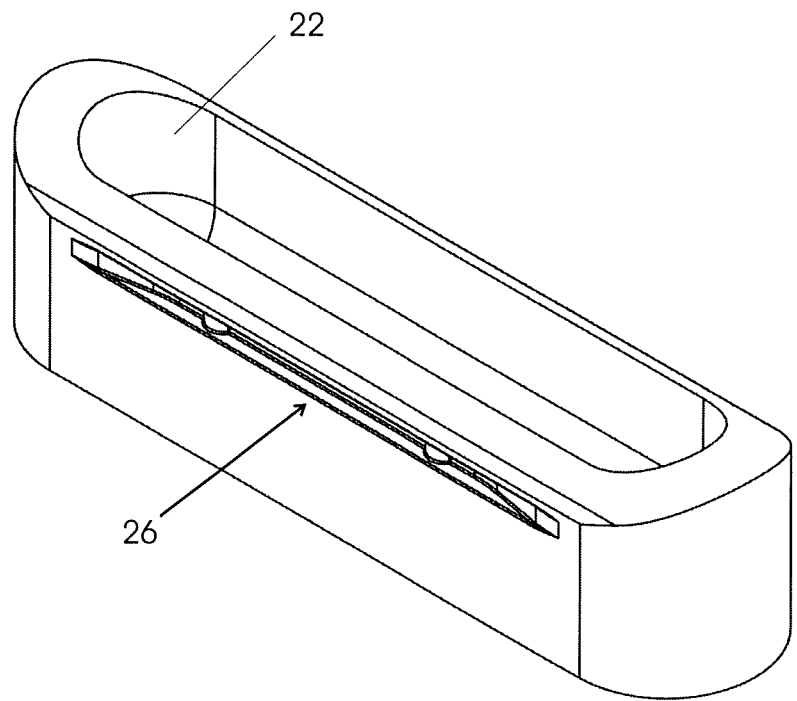
Figure 1(l)

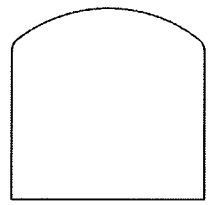
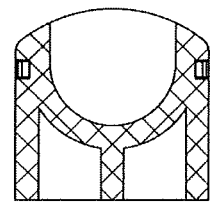
Figure 2(d)       Figure 2(e)
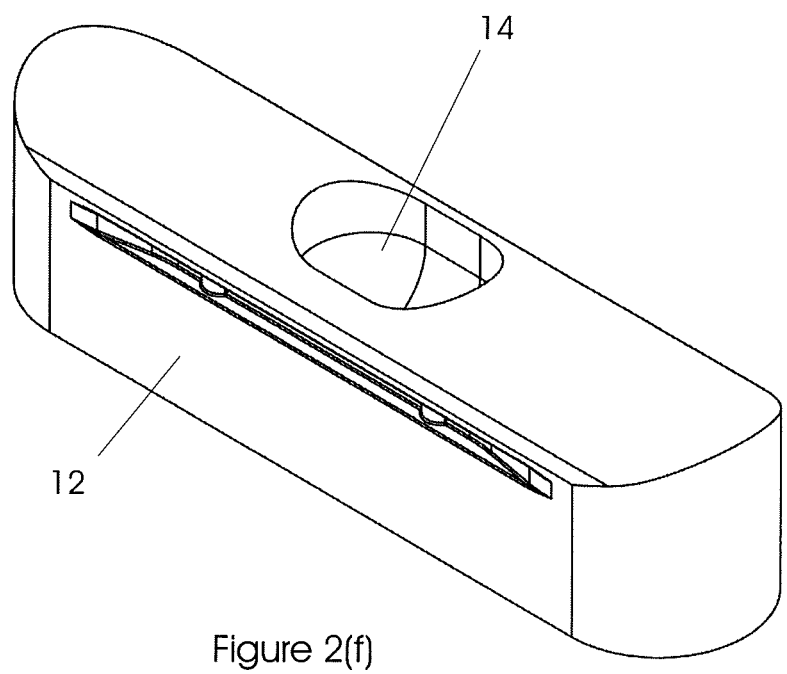
Figure 2(f)

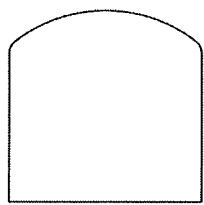 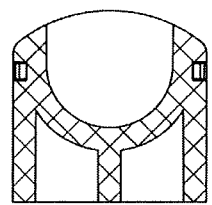
Figure 3(d)　　　　　　　　Figure 3(e)
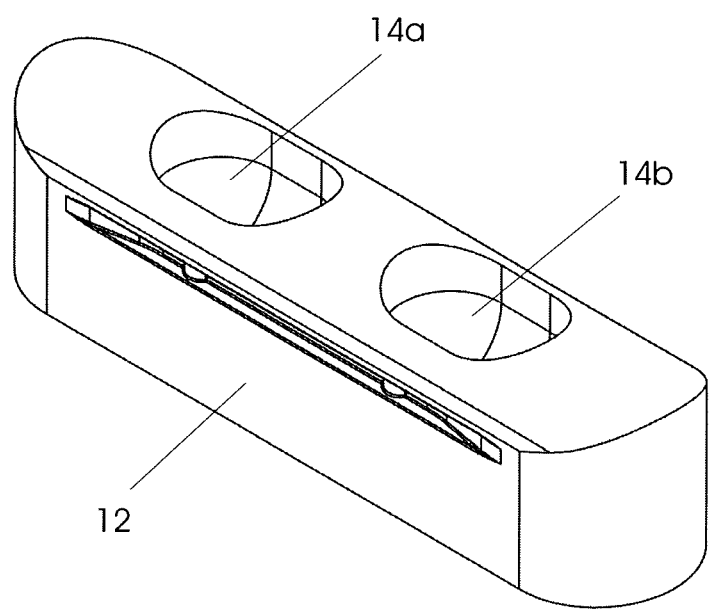
Figure 3(f)

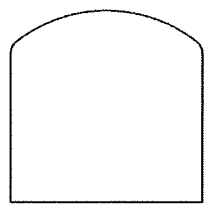
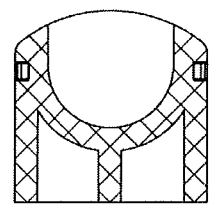
Figure 4(d)
Figure 4(e)
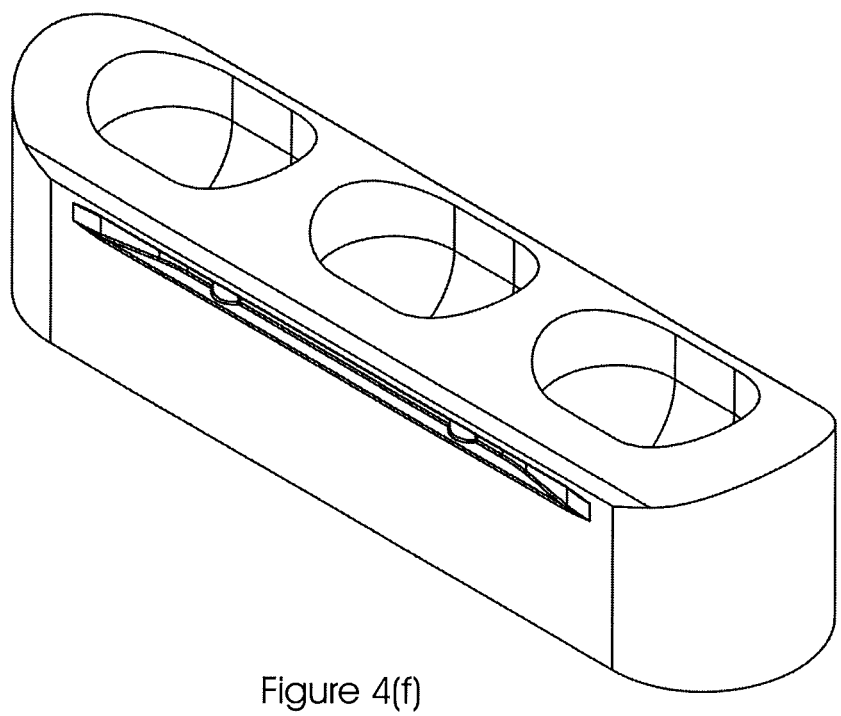
Figure 4(f)

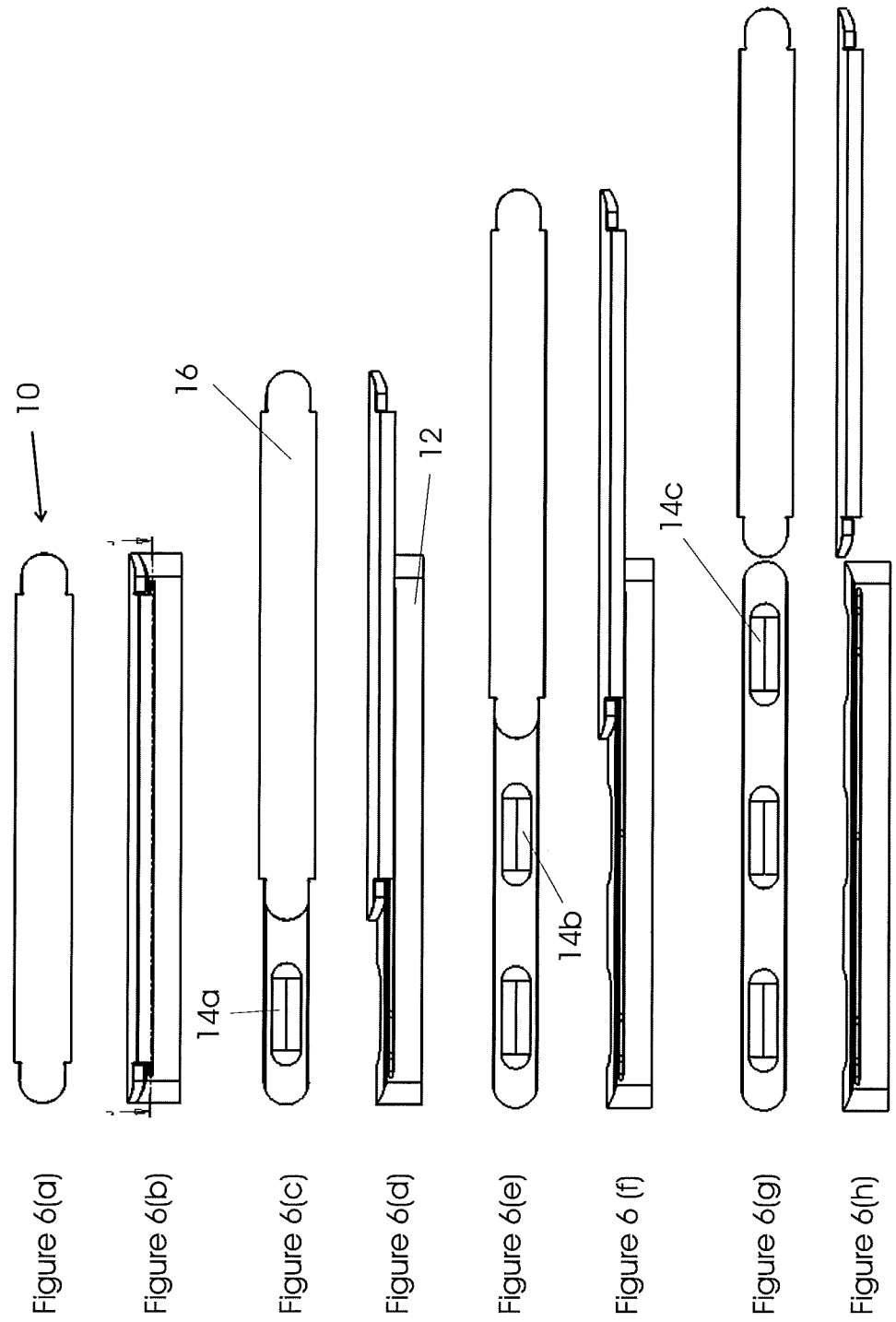

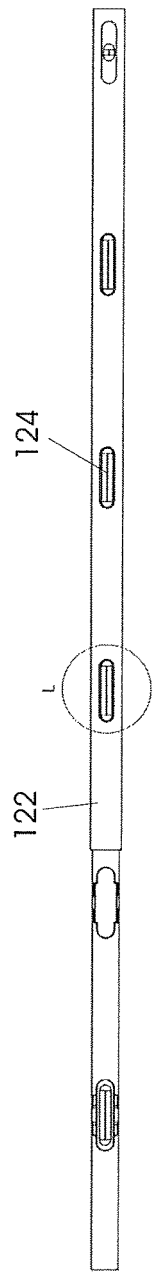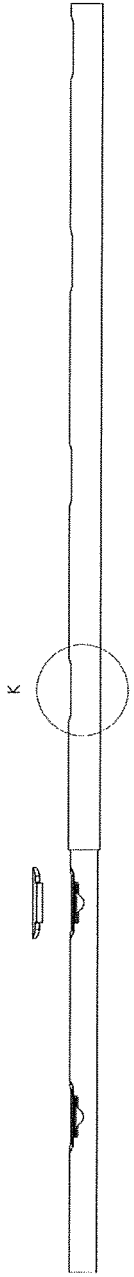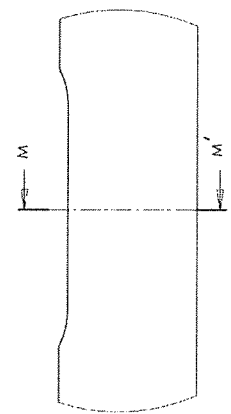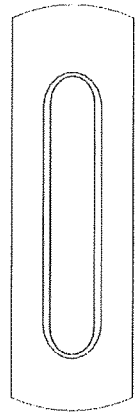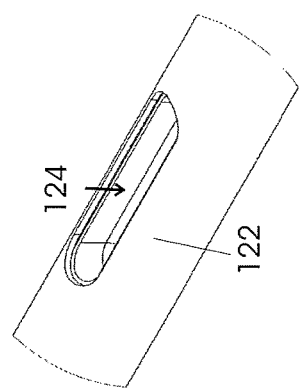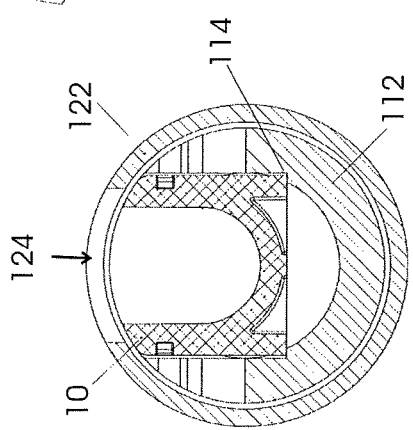

130
114

114

SAMPLING POD SYSTEM HAVING REMOVABLE SAMPLING POD WITH LID

TECHNICAL FIELD

The present invention concerns a sampling pod system and method of use; in particular for sampling solids; semi-solids, creams; and all forms of liquids, using a type of sampling tool commonly known as a "sampling thief".

BACKGROUND ART

Sampling tools such as "sampling thieves" are commonly used to sample granular materials and the like, and also liquids such as oils. Sometimes materials being sampled are potentially hazardous to human beings or to the environment. Typically, following sampling of a solid or liquid, the sample is transferred (usually manually) to a sample container, in which it is kept during transfer/transport to the location where it is analysed. Such transfer (from the sampling thief) can be time consuming, especially when stringent safety precautions need to be taken. Also, sometimes during such transfer the sample can become contaminated, or can contaminate the environment. Such transfer can also result in changes in the average sample composition (sample error); for example, retention (after sample transfer), of fine particles on the sampling pod inner surface, where a solid material is being sampled and the composition varies with particle size.

Sample thieves typically comprise a sample rod/tube configured to accommodate one or more open-topped sample pods and means of entirely enclosing the sample pod within the rod/tube; typically using a moveable outer sleeve, that in use surrounds the main body of the rod and also any sample pods held within. In use, following transfer of the sampled material (see above), the pods are typically cleaned and re-used.

DISCLOSURE OF INVENTION

The present invention aims to provide an improved apparatus and method of sampling granular (and the like) solids and also liquids; especially viscous liquids. A further aim/objective is to provide an apparatus and a method that allow safer, and simpler/faster transport of samples to a location for analysis than known systems; and also reduce the risk of environmental contamination and associated risk to operators, when sampling hazardous materials. Further aims are: to reduce the chance of samples being contaminated during the overall sampling and analysis process; and to reduce sample error by minimizing transfer of the sample between vessels, prior to an analysis.

In one aspect the present invention comprises a sampling tool sampling pod having a main body portion with at least one sample collecting cavity and a removable/opening lid portion that in use fits/closes over at least part of said main body portion and thereby covers said at least one cavity. Preferably, the lid portion also substantially seals said at least one cavity.

Preferably, the lid portion snap-fits over or slide-fits onto said main body portion; preferably, by engaging grooves or indents located along the upper side edges of the body portion. This advantageously allows the sample to be rapidly sealed following the taking of a material sample. Alternatively, the lid portion may be pivotally mounted/hinged to the main body portion. The lid portion can also be attached/secured to the main body by: magnetic means; by a screw/bolt (particularly if the sampling pod is circular); or by heat sealing.

In another aspect the invention comprises a sampling tool having a sampling rod with at least one sampling pod receiving cavity wherein said at least one receiving cavity is configured to receive a sampling pod according to the invention and where said receiving cavity allows said lid portion to be attached to said main body portion after sampling and prior to removal of said sampling pod from said sampling rod.

Preferably, the sampling tool receiving cavity further comprises at least one recess located on the upper portion of a side or end wall of the cavity that facilitates removal of said lid portion by a user. Preferably, the recess further comprises an approximately semi-circular ledge portion configured to assist manual removal by a user locating a thumb or index finger therein to grip part of a side portion of said sampling pod.

In another aspect the present invention comprises a method of sampling taking a solid or liquid sample using a sampling tool and/or sampling pod main body comprising the following steps: (a) Inserting said sampling pod main body within a sampling rod and taking a solid or liquid sample from a vessel/container containing said solid or liquid; (b) removing sampling rod from said vessel or container and covering said collecting cavity to substantially seal said cavity; (c) transporting said sample within said sampling pod to place of a analysis; and (d) at place of analysis removing at least part of said covering from main body portion to expose sample for analysis.

In another aspect the invention comprises a method of taking a solid or liquid sample using a sampling tool and/or sampling pod according to the invention comprising the following steps: (a) Inserting said sampling pod main body within a sampling rod and taking a solid or liquid sample from a vessel or container containing said solid or liquid; (b) removing sampling rod from said vessel or container and fitting a lid portion or other sealing means onto said main body portion over said collecting cavity to cover and/or seal said cavity; (c) transporting said sample within said sampling pod to place of analysis; and (d) at place of analysis, removing the lid portion from the main body portion to expose the sample for analysis. The lid portion may be held in place (fitted to the main body) by sliding onto grooves located on the outside edge of the main body; by snap-fitting onto grooves or indents located on a side face of the main body; by impulse sealing the lid; by adhesive; by magnetic means; by heat sealing; by a screw/bolt; and by sealing tape. The other sealing means may comprise encapsulating the main body portion with a plastics film or the like.

BRIEF DESCRIPTION OF THE DRAWINGS

The following diagrammatic drawings illustrate salient features of the present invention, where:

FIGS. 1(a) to 1(l) show a preferred embodiment of apparatus according to the present invention: FIG. 1(a) shows a side elevation of a sample pod (with a lid in place); FIG. 1(b) a corresponding plan view; FIG. 1(c) a sectioned plan view along the line 1-1'; FIG. 1(d) is a perspective view; and FIG. 1(e) is a sectioned side view along the line H-H'. FIG. 1(f) shows a side elevation of the main body portion of the sample pod; FIG. 1(g) a corresponding plan view; FIG. 1(h) is an underside view; FIG. 1(i) a sectioned plan view along the line D-D'; FIG. 1(*j*) is an end view; FIG. 1(*k*) is a sectioned side view along the line C-C'; and FIG. 1(*l*) is a perspective view.

FIG. 2(*a*) shows a side elevation of the main body portion of the sample pod; FIG. 2(*b*) a corresponding underside view; FIG. 2(*c*) is a sectioned side view along the line C-C'; FIG. 2(*d*) is an end view; FIG. 2(*e*) a sectioned plan view along the line B-B'; and FIG. 2(*f*) is a perspective view.

FIG. 3(*a*) shows a side elevation of the main body portion of the sample pod; FIG. 3(*b*) a corresponding plan view; FIG. 3(*c*) an underside view; FIG. 3(*d*) is an end view; FIG. 3(*e*) is a sectioned side view along the line C-C'; and FIG. 3(*f*) is a perspective view.

FIG. 4(*a*) shows a side elevation of the main body portion of the sample pod; FIG. 4(*b*) a corresponding plan view; FIG. 4(*c*) an underside view; FIG. 4(*d*) is an end view; FIG. 4(*e*) is a sectioned side view along the line E-E'; and FIG. 4(*f*) is a perspective view.

FIGS. 6)*a*) to 6(*h*) show various views of the sampling pod of FIG. 5 as the lid/cover is progressively slid open;

FIG. 8(*b*) shows a sectioned side view along the line J-J' of FIG. 8(*a*); and FIG. 8(*c*) shows a perspective view of the same part of a sampling rod etc.

FIG. 9(*b*) shows a corresponding side view; FIG. 9(*c*) shows an enlarged side view portion of the sampling tool (circle K of FIG. 9(*b*)); FIG. 9(*d*) shows an enlarged plan view of portion of the sampling tool (circle L of FIG. 9(*a*)); FIG. 9(*e*) shows a perspective view of the portion of the sampling tool shown in FIGS. 9(*c*) and 9(*d*); FIG. 9(*f*) shows a sectioned side view along the line M-M' of FIG. 9(*c*); FIG. 9(*g*) shows a plan view of the sampling tool with it's outer cover (with extra details); FIG. 9(*h*) shows a sectioned side view (along the lines O-O') corresponding to FIG. 9(*g*); FIG. 9(*i*) shows an enlarged plan view of portion of the sampling tool (circle Q of FIG. 9(*h*)); FIG. 9(*j*) shows an enlarged sectioned side view view of portion of the sampling tool (circle P of FIG. 9(*h*)); and FIG. 9(*k*) shows an enlarged perspective view of the portion of the sampling tool shown in FIGS. 9(*i*) and 9(*j*).

DETAILED DESCRIPTION OF THE INVENTION

Figure 1A:
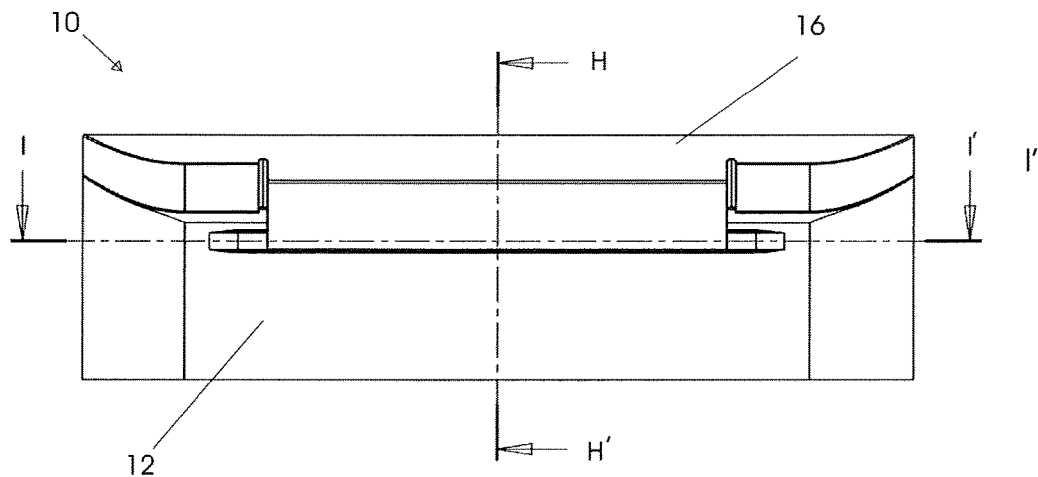
Figure 1B:
Figure 1C:
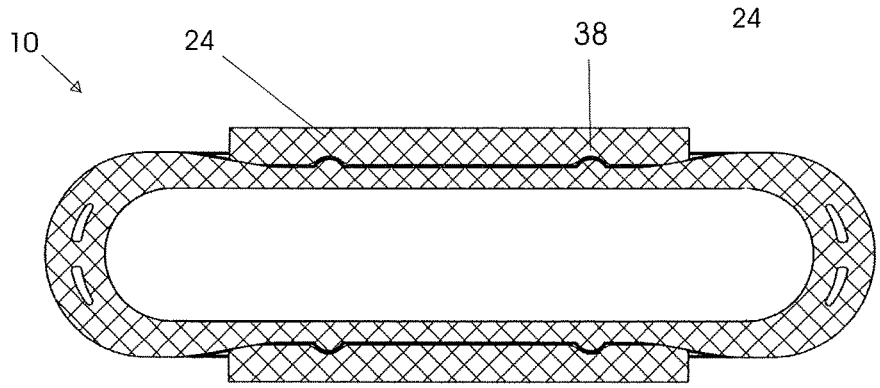
Figure 1D:
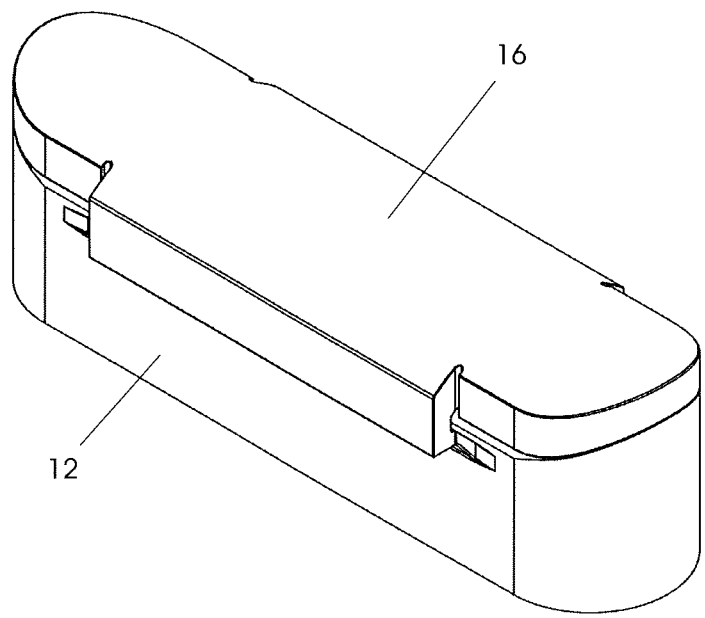
Figure 1E:
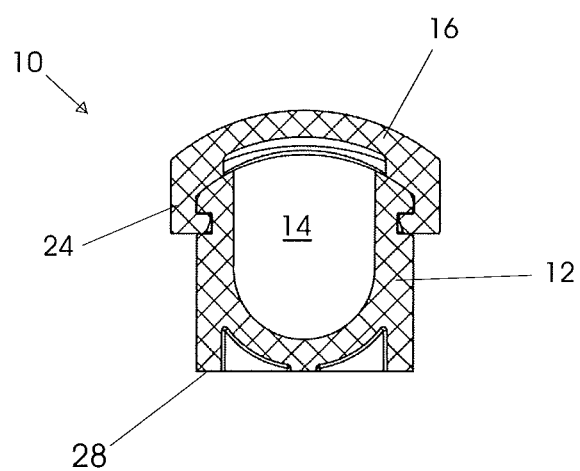
Figure 1F:
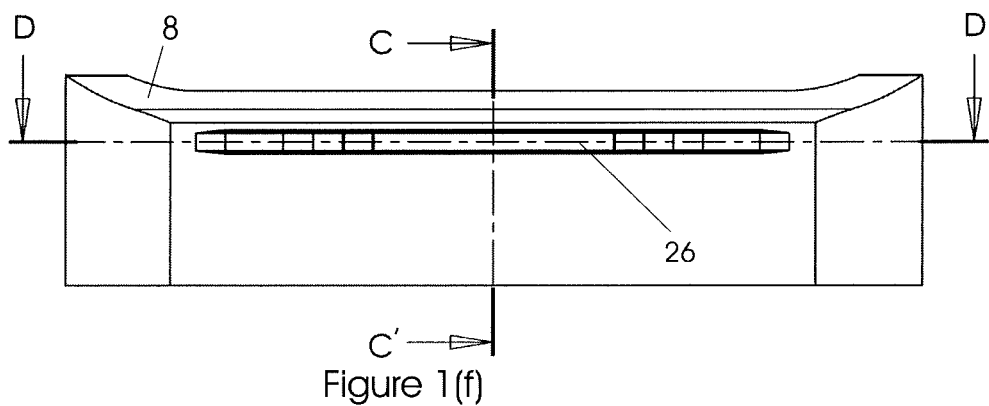
Figure 1G:
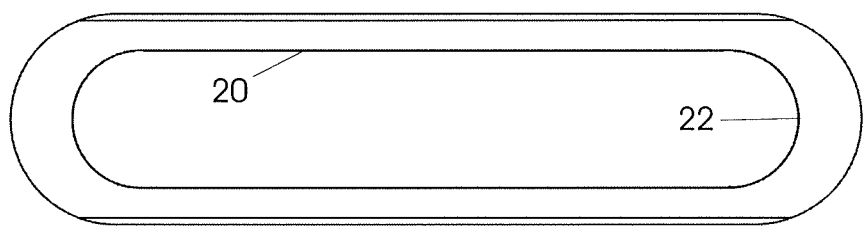
Figure 1H:
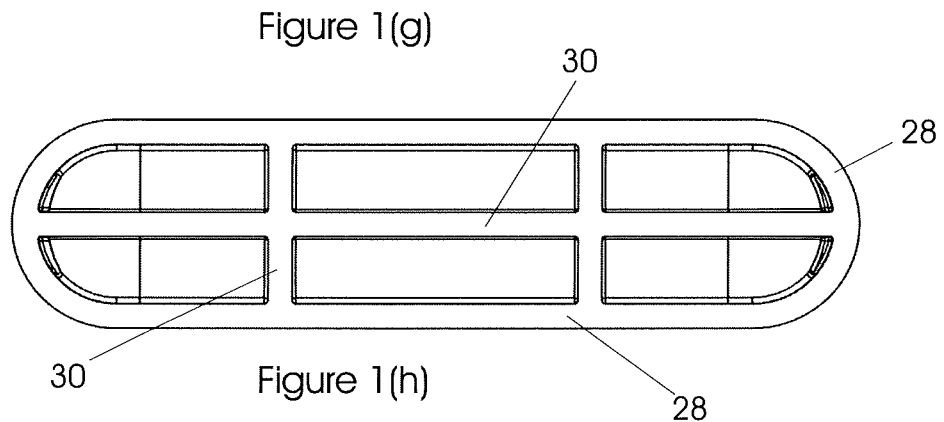
Figure 1I:
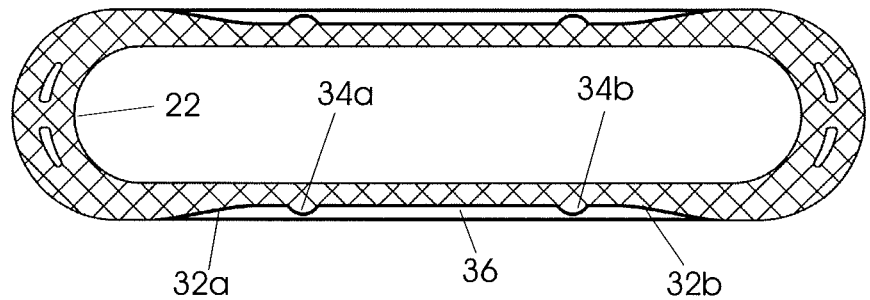

A preferred embodiment of the present invention is diagrammatically illustrated in FIGS. 1(*a*) to 1(*l*). These figures illustrate either a complete sampling pod (FIGS. 1(*a*) to 1(*e*)) or just the main body portion of the same sample pod (FIGS. 1(*f*) to 1(*l*)).

The sample pod (10) comprises a main body portion (12) and a lid portion (16). The main body portion (12) has a sample collecting cavity (14) bounded by a curved floor face (18); vertical flat side faces (20); and two curved end faces (22) and a curved (as viewed from side) top face (8). The lid portion (16) can be detached from the main body portion (12) to reveal the sample collecting cavity (14); which has an open top. The sampling pod is preferably made from a plastics material and preferably the lid portion is a softer or more compliant material than that used for the main body portion; this facilitates a snap-fit attachment by means of overhanging side members (24) integrally formed with the lid (16) and extending first sideways; then downwards and finally inwards; these side members (24) being configured to engage a pair of linear horizontal grooves (26) one located on an upper portion of each outside side face of the main body. Thus, when the lid portion (16) is attached to the main body (12) it covers, and at least substantially seals, the otherwise open top of the sampling collecting cavity (14) and thereby prevents loss of any solid or liquid that has been sampled before its attachment.

FIG. 1(*h*) shows an underside view of the main body portion (12) and in particular the underside feet/edge portions (28) located around the circumference of the base. In addition there are several cross members (30) the ends of which adjoin the feet/ledge portions (28). The number of cross members will vary according to the size of the sample pod and the material used to fabricate the pod. The depth of these cross members may also vary as the depth of the sample collecting cavity (14) varies, being deepest when the sample collecting cavity is most shallow. The size of the sampling pod (10) will vary according to the type of material being sampled etc.

FIG. 1(*i*) shows a sectioned plan view (along the lines D-D' of FIG. 1(*f*)) and shows that the linear horizontal grooves (26) on the side faces of the main body portion (12) comprise a first ramped portion (32*a*), a first notch (34*a*); a linear portion (36); a second notch (34*b*) and a second ramped portion (32*b*). The lid portion (16) can either be slid on or snap-fit engaged; in either case the lid portion (16) will normally be removed by sliding it along the linear grooves (26). When the lid portion (16) is in a fully-located position (covering/sealing the sample cavity) the notches (34) engage corresponding recesses (38) in the overhanging side members (24), and thereby prevent accidental movement of the lid.

Figure 2A:
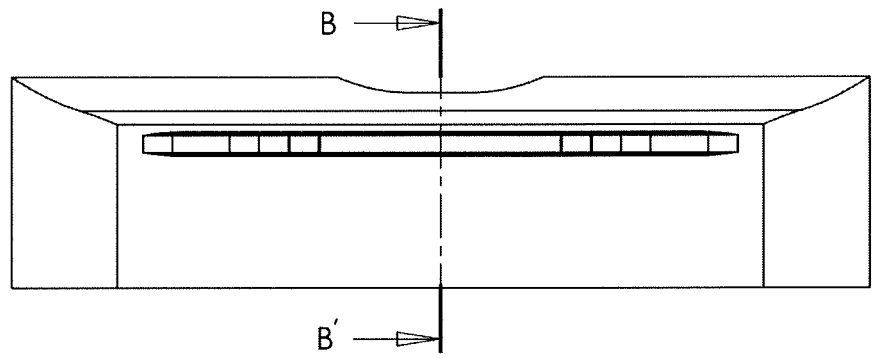
FIGS. 2(*a*) to 2(*f*) show the main body portion of a sampling pod according to a second embodiment of the present invention, with a single smaller and shallower sample-containing aperture.
Figure 2B:
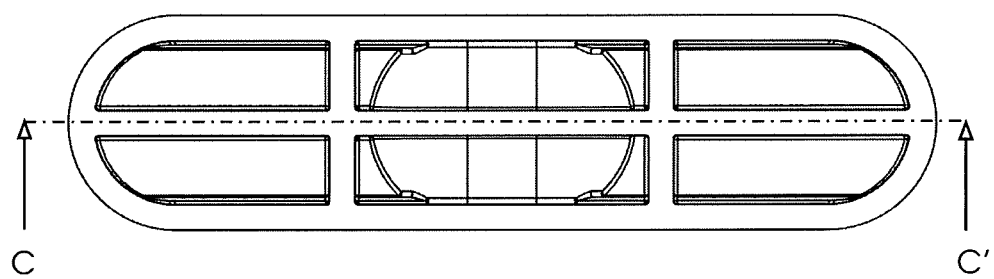
Figure 2C:
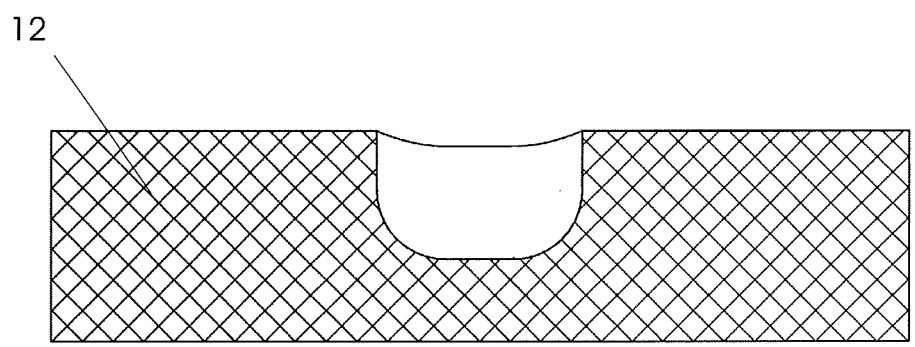

FIGS. 2(*a*) to 2(*f*) diagrammatically illustrate the main body portion (12) of a second embodiment of the invention. This embodiment has a sample collecting cavity (14) that is significantly shorter and shallower than that illustrated for the first embodiment; this cavity being located centrally (lengthwise) on the top face of the main body portion (12). The lid portion (16) is the same as that illustrated above for the first embodiment.

Figure 3A:
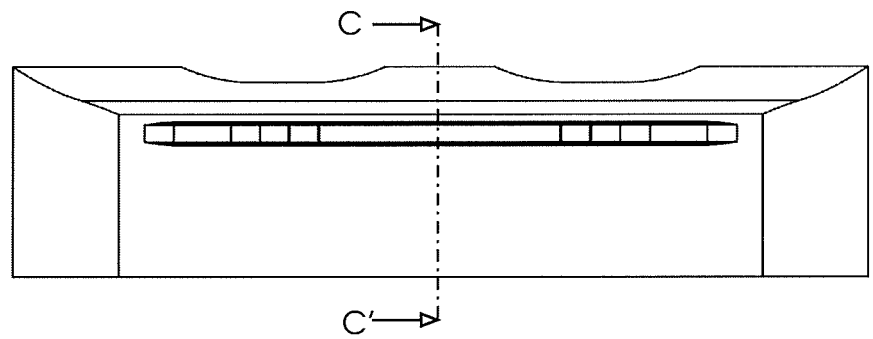
FIGS. 3(*a*) to 3(*f*) show the main body portion of a sampling pod according to a third embodiment of the present invention, with two sample-containing apertures.
Figure 3B:
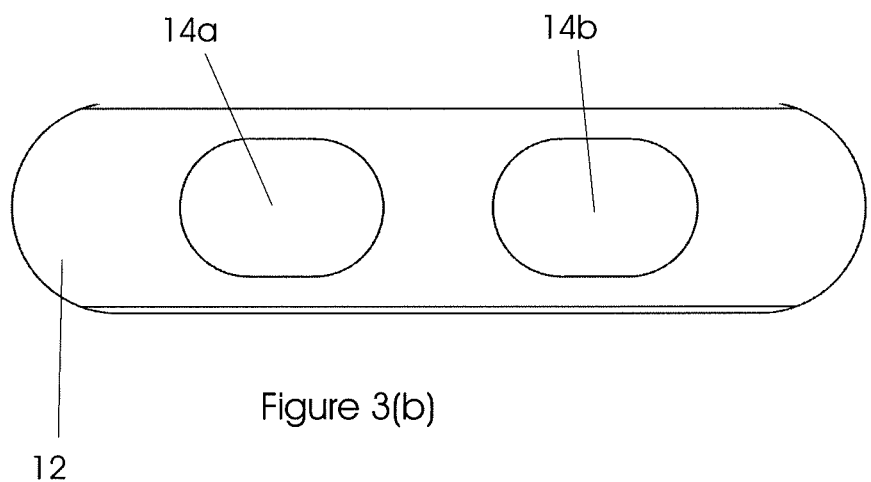
Figure 3C:
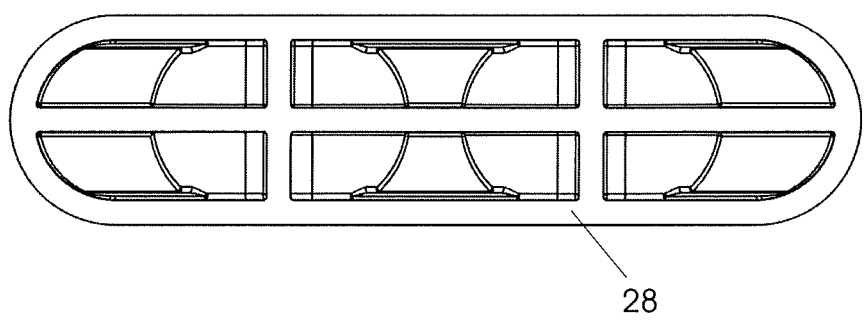

FIGS. 3(*a*) to 3(*f*) diagrammatically illustrate the main body portion (12) a third embodiment of the invention. This embodiment has two sample collecting cavities (14*a*, 14*b*) located in spaced-arrangement (lengthwise) on the top face of the main body portion (12). Again, the lid portion (16) is the same as that illustrated above for the first embodiment.

Figure 4A:
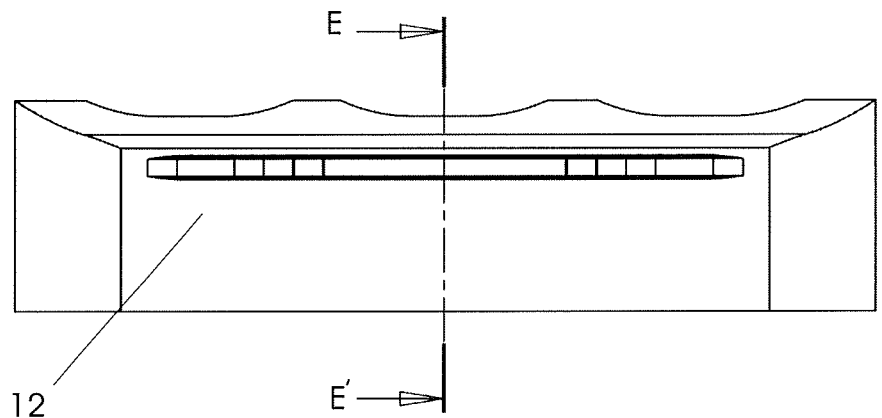
FIGS. 4(*a*) to 4(*f*) show the main body portion of a sampling pod according to a fourth embodiment of the present invention, with three sample-containing apertures.
Figure 4B:
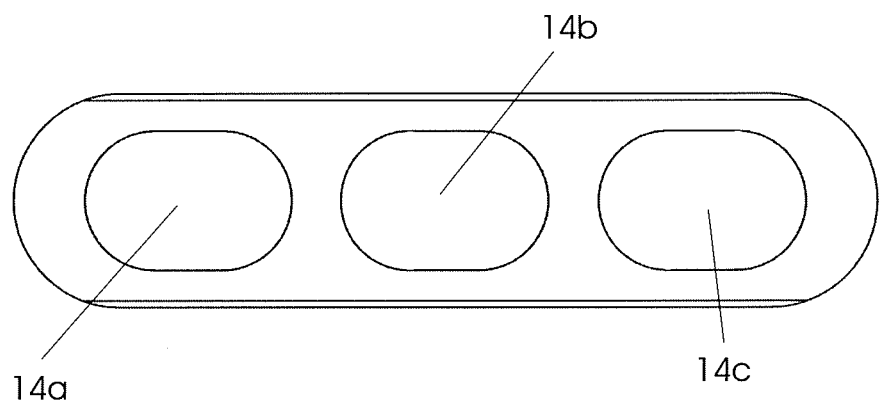
Figure 4C:
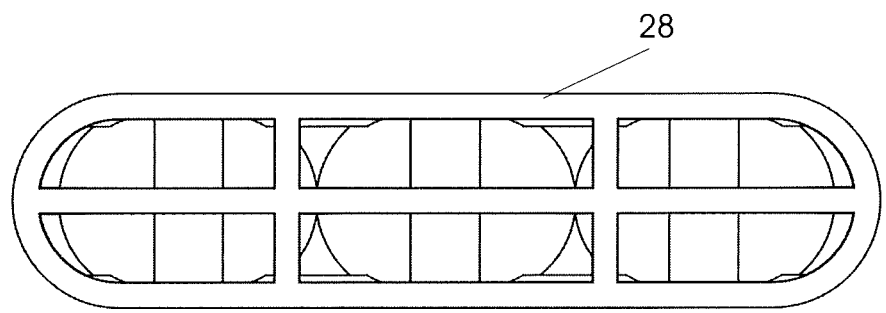

FIGS. 4(*a*) to 4(*f*) diagrammatically illustrate a fourth embodiment of the invention. This embodiment has three sample collecting cavities (14*a*, 14*b*, 14*c*) located in spaced-arrangement (lengthwise) on the top face of the main body portion (12). Each of these cavities (14) are shallower than the cavities illustrated in earlier embodiments.

Figure 5:
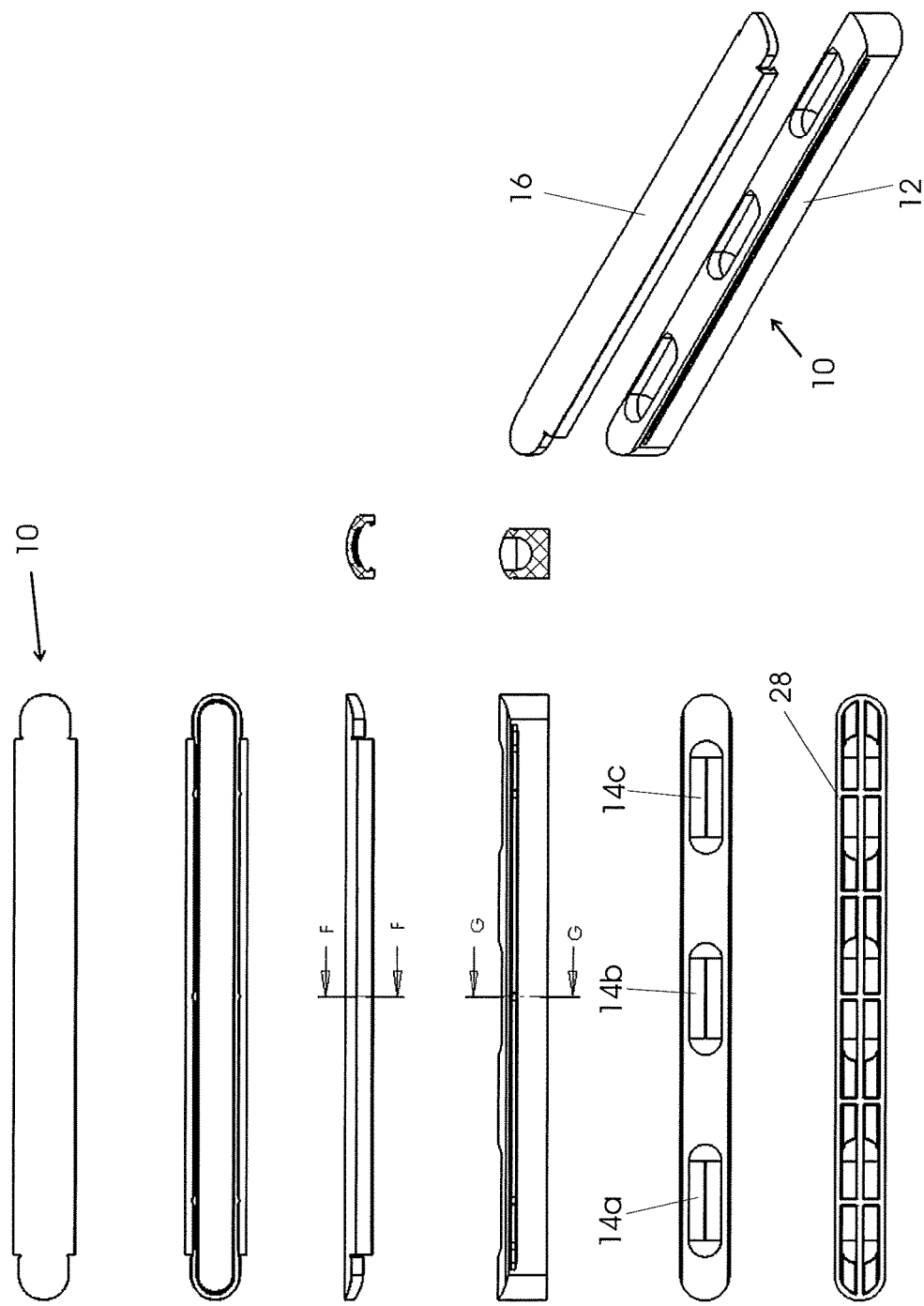
FIG. 5 shows various views of a sampling pod according to a fifth embodiment of the invention, having three sampling cavities spaced apart to facilitate sample removal.

FIG. 5 shows a fifth embodiment of the invention, the sampling pod (10) again having three sample collecting cavities (14a, 14b and 14c), but separated by a greater distance than the sampling pod illustrated in FIGS. 4(a) to 4(f). This greater separation facilitates removal of the sampled material (just prior to analysis) as the lid portion (16) is progressively slid open, as described below (see FIG. 6).

FIG. 6 shows the sampling pod (10) of FIG. 5 with the lid portion (16) in four different positions: FIGS. 6(a) and 6(b) show the lid sealing all three cavities (as it would during transfer to the location of analysis); FIGS. 6(c) and 6(d) with the lid portion (16) one third open (to allow the removal of the sampled material from first sample collecting cavity 14a; FIGS. 6(e) and 6(f) with the lid portion (16) two thirds open, to allow the (subsequent) removal of the sampled material from the second collecting cavity 14b; and FIGS. 6(f) and 6(g) show the sampling pod (10) with the lid portion (16) removed, to allow (last stage) the removal of sampled material from the third sample collecting cavity (14c).

Figure 7A:
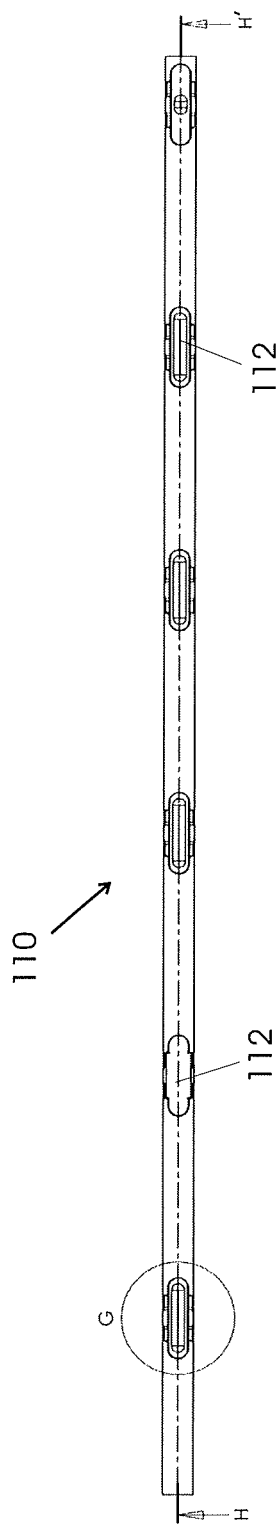
FIG. 7(*a*) shows a plan view of part of a sampling rod (without an outer cover) according to the present invention.
FIG. 7*b* shows a sectioned side view along the line H-H'.
Figure 7B:
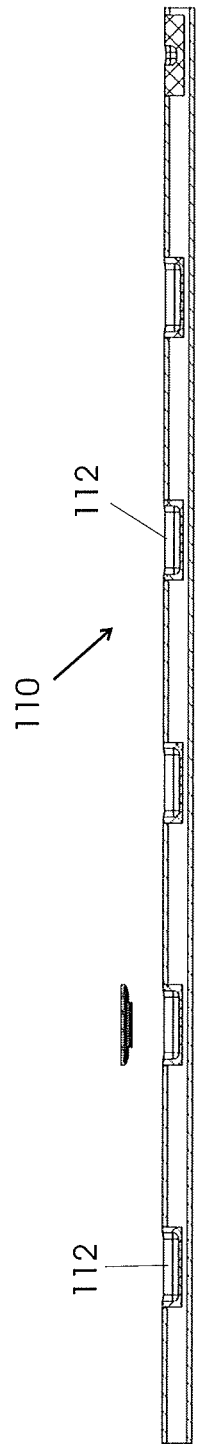

FIGS. 7(a) and 7(b) show a simple sampling rod (110), less the outer cover (see below) having several sampling pod (10) receiving cavities (112) located along the longitudinal axis of the rod; and in this case equally spaced along the sampling rod. The size of the sample receiving cavities (112) will vary according to the size of the sampling pod (10) being used and also the spacing of the cavities will vary according to sampling requirements (depth-wise). In some cases the spacing may be irregular (rather than the evenly spacing illustrated).

Figure 8A:
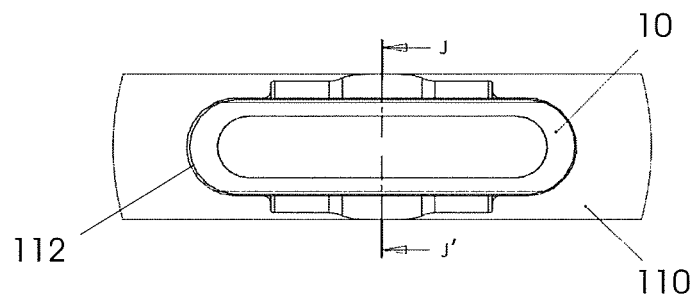
FIG. 8(*a*) shows an enlarged plan view of that part of a sampling rod circled G in FIG. 7(*a*) with the sampling pod fitted within a sampling pod receiving cavity.
Figure 8B:
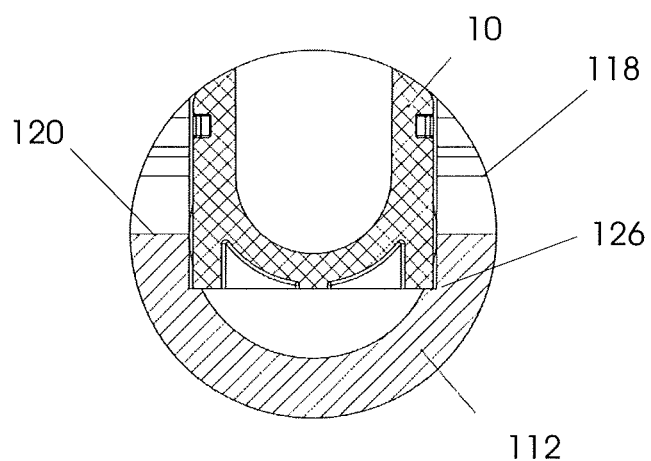
Figure 8C:
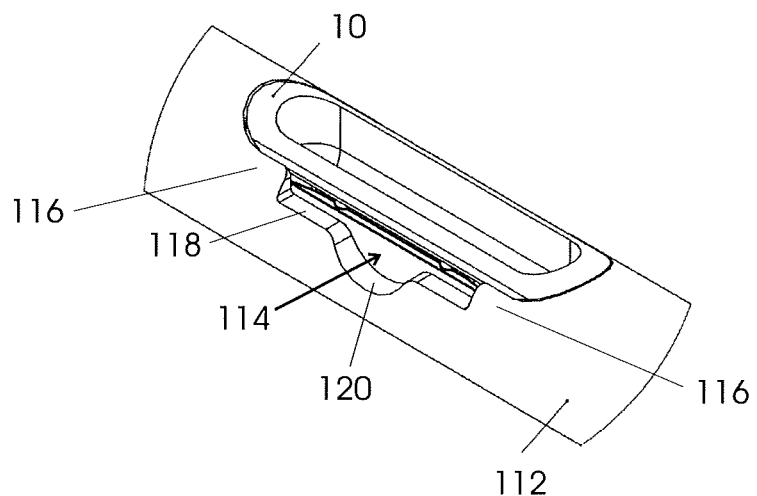

FIG. 8(a) shows one receiving cavity (circled G in FIG. 7(a)) in enlarged detail, containing a sampling pod (10); and FIG. 8(b) shows a sectioned end view of the sampling rod (110) and sampling pod (10), along the lines J-J' of FIG. 8(a). FIG. 8(c) shows a perspective view corresponding to FIGS. 8(a) and 8(b). The sampling rod (110) is made of tubular material (e.g. stainless steel) and the inside of the tube has a pair of shelves (114) upon which the underside feet (28) of the sampling pod (10) rest and support the pod within the tube (110). The sampling pod (10) is further held in place by four side-wall portions (116) of the receiving cavity (112); two on each side. Between the pair (on each side) is an indent/recess (114) comprising a pair of flat edges (118), located either side of an approximately semi-circular (as viewed from side) ledge (120). Preferably, these recesses include "finger engaging" portions the purpose of which is to readily allow a user to pull the sampling pod (10) out of the sampling rod/tube cavity (112) after a lid has been fitted (to seal the sampled material within the pod). Thus, the combination of these two features (118, 120) provides an indent/recess (114) that facilitates manual (hand finger or thumb) placement in and removal of the sampling pod (10) from the sampling rod (110).

FIGS. (a) to 9(k) show part of a sampling tool having an outer sleeve (122) which can be rotated about the longitudinal axis of the rod/sleeve by means of a handle (not illustrated). The outer sleeve (122) has at least one aperture (124) that corresponds in size and shape to the open top face of the sample collecting cavity (14). In use by rotating the outer sleeve (122) relative to the tube/rod 110 the sample collecting cavities can be exposed; thus allowing sample material to enter the sample collecting cavities.

Figure 9G:
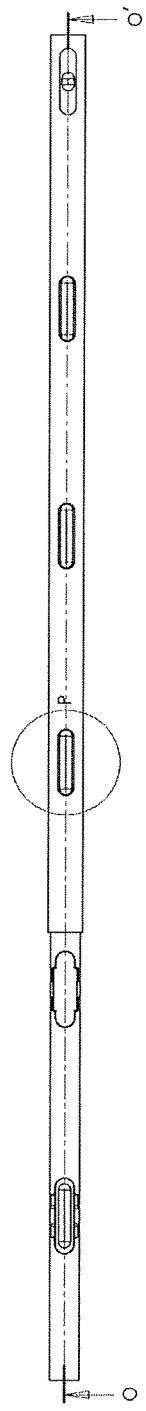
FIG. 9(*a*) shows a plan view of a part of a sampling tool (but with outer cover) according to the present invention.
Figure 9H:
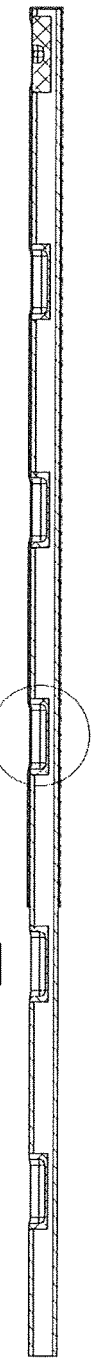
Figure 9K:
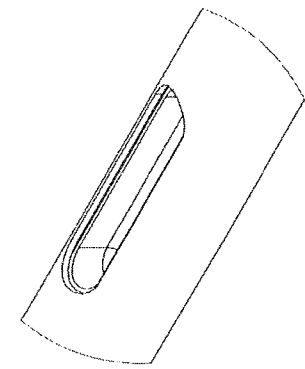
Figure 9I:
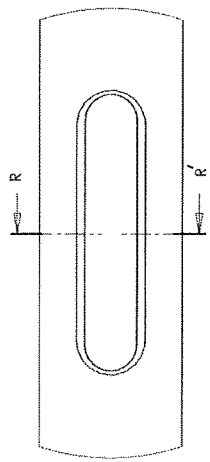
Figure 9J:
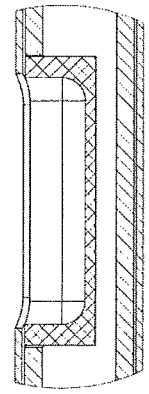

FIG. 9(f) shows how the main body portion (12) can be contained within a sampling rod/tube (110) and outer sleeve (122). The rod/tube has at least one cavity (112) sized to provide a snug fit for the sampling pod. Preferably, each cavity has at least one side indent/recesses (114) that facilitate said receiving of lid portion (16) and/or removal of said lid portion by a user. These recesses (114) also allow the lid portion (12) to be attached (e.g. by snap-fit) to the main body portion (12) while the main body portion is still within the sampling rod/tube (110). The top face (8) of the sampling pod main body portion (12) has a curvature (seen from side view) that matches the curvature of the inner surface of the outer sleeve (122); thus allowing the sampling pod (10) to fit snugly within the sampling tool; and in particular the outer sleeve (122) during rotation.

Figure 10B:
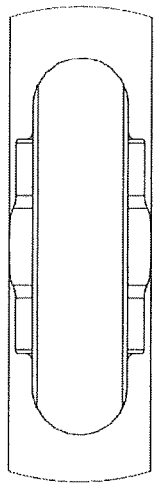
FIG. 10 shows details of sampling pod receiving cavities for further embodiments of the invention having various indent/recess configurations, etc.
Figure 10D:
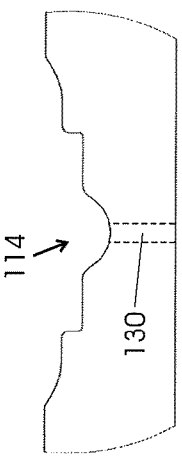
Figure 10F:
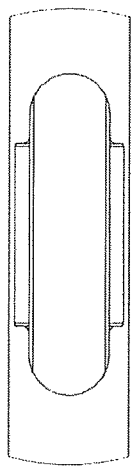
Figure 10H:
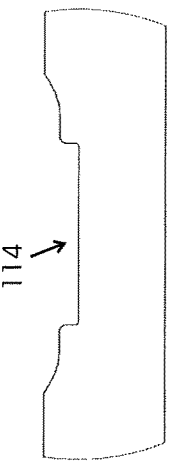
Figure 10A:
Figure 10C:
Figure 10E:
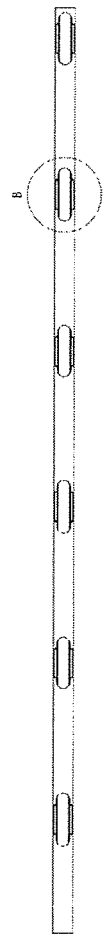
Figure 10G:

FIGS. 10(a) to 10(d) and 10(e) to 10(h) show two alternative configurations (respectively) for the recesses (114) and also an embodiment (see FIG. 10(d)) where a cylindrical aperture (130) is provided to facilitate removal of a sampling pod main body portion (12) using a tool (such as a screwdriver) inserted through the underside face of the sampling pod such to push the sampling pod (10) upwards by applying force to the base of the main body portion (12).

In a further aspect of the method of the invention, after collecting a material sample the sampling pod is sealed by a self-adhesive film or by a shrink-wrapped covering prior to being transported in the thus-sealed pod to a location where it is analysed. At the time of analysis the sample is released either by removing the film or puncturing of the covering and then removing the material sample.

Discrete sampling pods are typically held in cavities/pockets (112) spaced (longitudinally) along a sampling tool/rod (110), and this spacing determines the depths that individual samples are taken when the tool/rod (110) is inserted within the material to be sampled. The Sampling pods have cavities/pockets (112) that may vary in size and can have one or more cavity per collecting pod. The cavities (112) may be unequal in size. The sampling pod (10) may be fabricated from various materials: e.g. polymer, metal, ceramics.

The sampling pod of the present invention provides various means of sealing the sampling cavity after sample collection. Typically, this is a lid/cover or the like, applied to the sampling pod when it is still within the tool/rod. Preferably, the lid/cover is fitted to the main body by a snap-fit action or by sliding engagement of grooves on an outside face of the main body. Preferably, the sampling pod (10) is made by moulding a plastics material, and the lid/cover portion (16) is similarly made, but using a more compliant/flexible plastics material; thereby providing enhanced containment performance.

Alternatively, after sampling the sampling pod cavity/cavities may be sealed by other means e.g. shrink-wrap covering, application of a self-adhesive film, sliding the sampling pod within a (surrounding) tube etc. In general, the sampling pod (10) will be made from materials able to withstand the chemical challenges of materials being sampled.

Upon arrival at the sample analysis location lid is removed or cover penetrated to allow recovery of the sampled material within. For example, the lid can be progressively slid off to reveal one or more samples. Alternatively, at this time, the sample may be removed for analysis using an automated sample handling systems. In this event it may be preferable to use a cover (such as shrink-wrap), rather than a lid, which can be punctured to allow the sample to be removed by an automated system. This is particularly desirable when hazardous materials are being sampled and analysed; providing greater protection (than the prior-art) to both the operators and the environment.

The apparatus and method of the present invention advantageously allow: simplified sample recovery; and reduces transfer errors. When the pod lid is fitted the closed pod provides a discrete container for the sampled material that is easy to handle. Preferably, sampling pods are only used one, and then disposed of, this eliminates cross contamination risk. However, if necessary they can also be reused following (where appropriate) sterilization and/or cleaning.

We claim:

1. A sampling tool comprising: a sampling pod, and
a sampling rod with a removable tubular outer sleeve that surrounds said sampling rod;
wherein said sampling rod has at least one pod receiving cavity configured to receive said sampling pod, so that, only during sampling, said sampling pod is housed within said pod receiving cavity and retained therein by said outer sleeve; and
wherein said sampling pod comprises a main body portion and an attachable/removable lid portion configured, after sampling and removal of said outer sleeve, to engage at least part of said main body portion, while the sampling pod is still housed within said pod receiving cavity, and thereby substantially seal said sampling pod.

2. The sampling tool according to claim 1, wherein said sampling pod main body portion comprises a plurality of sampling cavities and said attachable/removable lid portion includes a single lid portion comprising a roof portion and two integrally formed side members, extending first sideways, then downwards and finally inwards, the side members being configured to engage a pair of linear horizontal grooves, one located on an upper part of each outside side face of the main body portion, thereby facilitating progressive removal of sampled material as said single lid portion is progressively slid open.

3. The sampling tool according to claim 1, wherein said lid portion comprises a roof portion and two integrally formed side members, extending first sideways, then downwards and finally inwards, the side members being configured to engage a pair of linear horizontal grooves one located on an upper part of each outside side face of the main body portion; and wherein the pod receiving cavity has at least one additional side indent/recess, provided to allow attachment of said lid portion to said main body portion after sampling; and subsequently assist a user to manually remove said sampling pod, with attached lid portion, from said sampling rod.

4. The sampling tool according to claim 1, wherein said lid portion comprises a roof portion and two integrally formed side members; extending first sideways, then downwards and finally inwards, the side members being configured to engage a pair of linear horizontal grooves one located on an upper part of each outside side face of the main body portion; and wherein the pod receiving cavity has at least one additional side indent/recess comprising a pair of flat edges, located either side of an approximately semi-circular ledge, configured to allow attachment of said lid portion to said main body portion after sampling and to subsequently assist a user to manually remove said sampling pod, with attached lid portion, from said sampling rod.

5. The sampling tool according to claim 1, wherein said sampling pod main body portion comprises a roof portion and two integrally formed side members, extending first sideways, then downwards and finally inwards, the side members being configured to engage a pair of linear horizontal grooves one located on an upper part of each outside side face of the main body portion; wherein said lid portion is made from a plastics material that is a more compliant material than that used for the main body portion so allowing the lid portion to snap-fit over said linear horizontal grooves of the main body portion.

6. A sampling pod comprising a main body portion that during sampling is housed within a pod receiving cavity formed within a sampling rod and retained therein by a removable tubular outer sleeve that operably surrounds said sampling rod; said sampling pod further comprises an attachable/removable lid portion configured, after sampling and removal of said outer sleeve, to engage and fit over at least part of said main body portion of said sampling pod, while the pod is still housed within said pod receiving cavity, and thereby substantially seal a collected sample within said sampling pod.

7. The sampling pod according to claim 6, wherein said sampling pod main body portion comprises a plurality of sampling cavities and a single lid portion comprises a roof portion and two integrally formed side members; extending first sideways, then downwards and finally inwards, the side members being configured to engage a pair of linear horizontal grooves one located on an upper part of each outside side face of the main body portion, thereby facilitating progressive removal of sampled material as said single lid portion is progressively slid open.

8. The sampling pod according to claim 6, wherein said sampling pod main body portion comprises a roof portion and two integrally formed side members, extending first sideways, then downwards and finally inwards, the side members being configured to engage a pair of linear horizontal grooves one located on an upper part of each outside side face of the main body portion; wherein said lid portion is made from a plastics material that is a more compliant material than that used for the main body portion so allowing the lid portion to snap-fit over said linear horizontal grooves of the main body portion.

9. The sampling pod according to claim 6, wherein said lid portion comprises a roof portion and two integrally formed side members, extending first sideways, then downwards and finally inwards, the side members being configured to engage a pair of linear horizontal grooves one located on an upper part of each outside side face of the main body portion; and wherein the pod receiving cavity has at least one additional side indent/recess, provided to allow attachment of said lid portion to said main body portion after sampling and removal of said outer sleeve, and subsequently assist a user to manually remove said sampling pod, with attached lid portion, from said sampling rod.

10. The sampling pod according to claim 6, wherein said lid portion comprises a roof portion and two integrally formed side members extending first sideways, then downwards and finally inwards, the side members being configured to engage a pair of linear horizontal grooves one located on an upper part of each outside side face of the main body portion; and wherein the pod receiving cavity has at least one additional side indent/recess comprising a pair of flat edges, located either side of an approximately semi-circular ledge, provided to allow attachment of said lid portion to said main body portion after sampling and removal of said outer sleeve, and subsequently assist a user to manually remove said sampling pod, with attached lid portion, from said sampling rod.

11. A sampling tool comprising a sampling pod, and a sampling rod with a removable outer sleeve that surrounds said sampling rod and has a sampling sleeve aperture and can be rotated about the longitudinal axis of said sampling rod, relative to said sampling rod: wherein said sampling rod comprises: at least one pod receiving cavity configured to receive said sampling pod, such that only during sampling, said sampling pod is housed within said pod receiving cavity and retained therein by said outer sleeve; a main body portion; and an attachable/removable lid portion configured to engage at least part of said main body portion and thereby substantially seal said sampling pod, after removal of said outer sleeve and while the pod is still housed within said pod receiving cavity.

12. The method of taking a solid or liquid sample using a sampling tool according to claim 11 said method comprising:
   (a) inserting said sampling tool containing said sampling pod retained by said surrounding outer sleeve within a vessel containing said solid or liquid to be sampled and collecting at least one sample in an exposed sampling pod main body potion via said sampling sleeve aperture;
   (b) removing said sampling tool from said vessel;
   (c) removing said surrounding outer sleeve from said sampling rod;
   (d) engaging said lid portion with at least part of said main body portion of said sampling pod to at least substantially seal said sampling pod; and
   (e) removing substantially sealed sampling pod from pod receiving cavity of said sampling rod prior to analysis of the at least one sample.

* * * * *